United States Patent [19]

Schreiber

[11] Patent Number: 5,075,321
[45] Date of Patent: Dec. 24, 1991

[54] METHODS OF TREATING DISEASES CHARACTERIZED BY INTERACTIONS OF IGG-CONTAINING IMMUNE COMPLEXES WITH MACROPHAGE FC RECEPTORS USING ANTIESTROGENIC BENZOTHIOPHENES

[75] Inventor: Alan D. Schreiber, Philadelphia, Pa.

[73] Assignee: University of Pennsylvania, Philadelphia, Pa.

[21] Appl. No.: 159,714

[22] Filed: Feb. 24, 1988

Related U.S. Application Data

[63] Continuation-in-part of Ser. No. 30,028, Mar. 24, 1987, abandoned, and a continuation-in-part of Ser. No. 89,790, Aug. 27, 1987, Pat. No. 4,902,681.

[51] Int. Cl.$^5$ ............................................. A16K 31/56
[52] U.S. Cl. .................................... 514/317; 514/319; 514/324
[58] Field of Search ...................... 514/317, 319, 324

[56] References Cited

U.S. PATENT DOCUMENTS 4,418,068  11/1983  Jones .

OTHER PUBLICATIONS

Nettl, et al., "The Effect of Endogenous And Synthetic Steroids On The Clearance Of IgG And/Or C3 Coated Cells", *Blood* 64: Suppl. 1:8A (Abstract) (1984).
Ahn, et al., "Danazol For The Treatment Of Idiopathic Thrombocytopenic Purpura", N. Engl. J. Med. 308: 1396–1399 (1983).
Schreiber, et al., "Effect Of Danazol In Immune Thrombocytopenic Purpura", N. Engl. J. Med. 316: 503–508 (02/26/87).
Dougados, et al., Arthritis Rheum. (Suppl) 28: 246 (1985).
Jungers et al., "Hormonal In Systemic Lupus Erythematosus", Arthritis Rheum. 28: 1234–1250 (1985).
Fretwell, et al., J. Allergy Clin. Immunol. 69: 306–310 (1982).
Schreiber, et al., "Role Of Antibody And Complement In The Immune Clearance And Destruction of Erythrocytes", J. Clin. Invest. 51: 575, 583–589 (1972).
Friedman, et al., "Effect Of Estradiol And Steroid Analogues On The Clearance Of Immunoglobulin G--Coated Erythrocytes", J. Clin Invest. 75: 162–167 (1985).
Atkinson, et al., "Effects Of Corticosteroids And Splenectomy On The Immune Clearance And Destruction Of Erythrocytes", J. Clin. Invest. 52(6): 1509–1517 (1973).
Sanders, et al. "Hormonal Modulation Of Macrophage Clearance Of IgG Sensitized Cells", Reprinted from the Transactions of the Association of American Physicians (Abstract), vol. C, pp. 268–275 (1987).

*Primary Examiner*—Nathan M. Nutter
*Attorney, Agent, or Firm*—Woodcock Washburn Kurtz Mackiewicz & Norris

[57] ABSTRACT

Clearance of antibody-coated cells from the circulation is modulated by administering an effective amount of certain benzothiophene derivatives, or the physiologically acceptable acid addition salts thereof. The compounds are useful in treating mammalian diseases characterized by interactions between IgG containing immune complexes and macrophage Fc receptors.

53 Claims, 2 Drawing Sheets

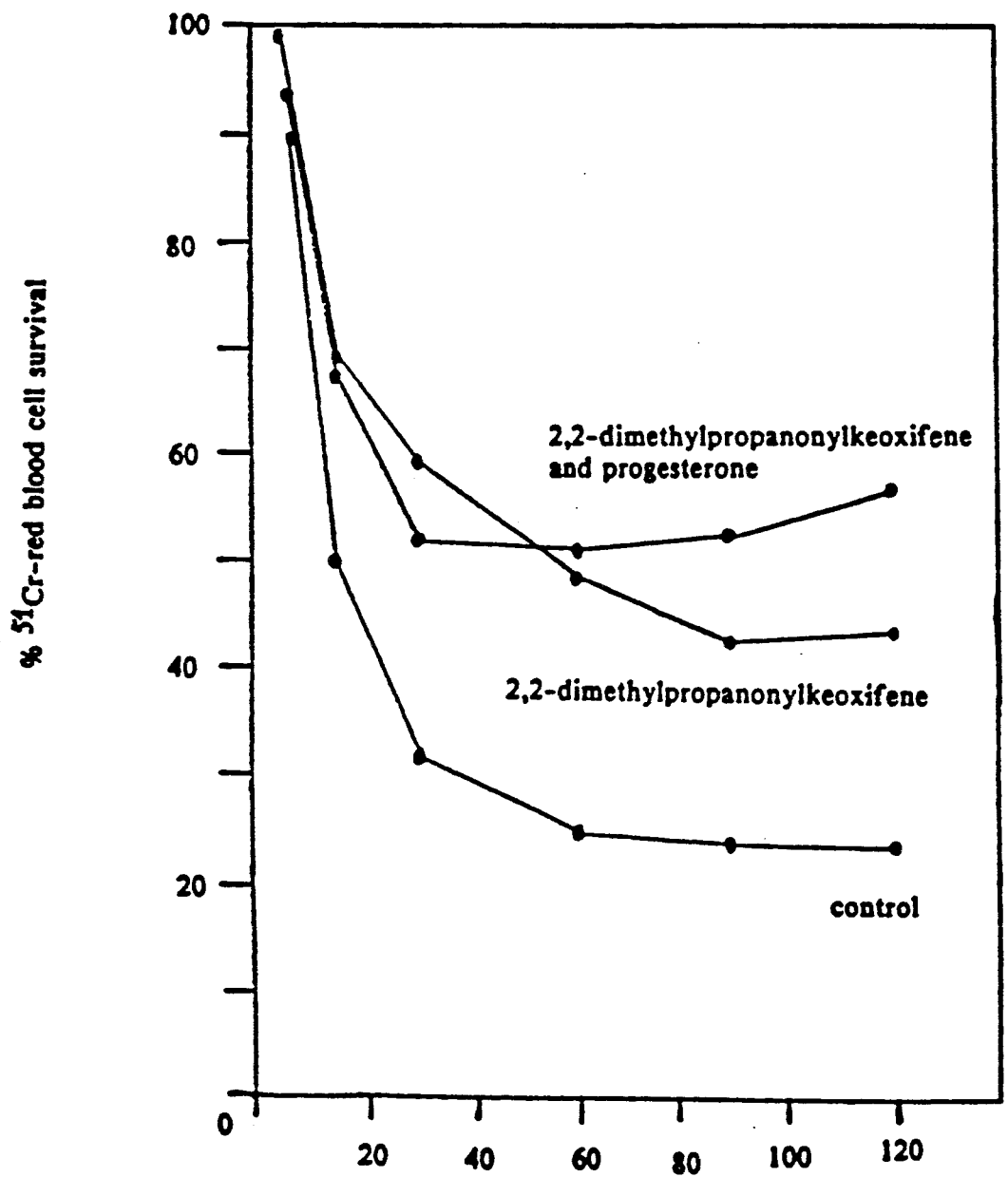

METHODS OF TREATING DISEASES CHARACTERIZED BY INTERACTIONS OF IGG-CONTAINING IMMUNE COMPLEXES WITH MACROPHAGE FC RECEPTORS USING ANTIESTROGENIC BENZOTHIOPHENES

REFERENCE TO GOVERNMENT GRANT

The invention described herein was supported by National Institute of Health grant AI22193. The Government has certain rights in the invention.

CROSS-REFERENCE TO RELATED APPLICATIONS

This application is a continuation-in-part of application Ser. No. 030,028 filed Mar. 24, 1987 now abandoned. This application is also a continuation-in-part of pending application Ser. No. 089,790, filed Aug. 27, 1987 and now U.S. Pat. No. 4,902,681.

FIELD OF THE INVENTION

The invention relates to the treatment of mammalian diseases characterized by interactions of IgG-containing immune complexes and macrophage Fc receptors, and in particular to the modulation of the clearance of antibody-coated cells from the circulation of mammals.

BACKGROUND OF THE INVENTION

Glucocorticoids have been widely employed in the treatment of immunologic disorders. Other steroid hormones, such as sex steroids, may also influence the clinical expression of immunologic disease. For, example, estrogens and their analogues have several known effects on the immune system. This group of sex hormones appears to increase the production of serum globulins, increase the phagocytic nature of mononuclear cells, increase the clearance of IgG-coated cells by splenic macrophages, and bind to and alter the functions of suppressor T-cells.

In autoimmune diseases such as thrombocytopenic purpurea (ITP) there is an increased clearance of platelets by macrophages in the spleen. ITP is believed to be caused by antiplatelet antibodies, which are frequently of the IgG class. These antibodies bind to the platelets forming IgG containing immune complexes. Levels of IgG on the platelet surface are generally elevated in patients with ITP; a change in the level of platelet-bound IgG in a given patient is often associated with a change in the platelet count with increases in bound IgG generally correlating with decreased platelet levels. The level of platelet-associated IgG, however, does not correlate uniformly with the platelet count in ITP. One explanation for this discrepancy may be differences in the rate or extent of clearance of platelets that is initiated by the adherence of IgG-coated platelets to surface Fc (IgG) receptors on tissue macrophages. For example, the rate of platelet clearance may be affected by processes that alter the capacity of macrophage Fc (IgG) receptors to recognize the IgG ligand.

In the spleen, IgG-containing immune complexes bind by the Fc region of IgG to macrophages at Fc receptor sites on the macrophage surface. The Fc portion of the immunoglobulin molecule (identified by papain cleavage) is believed to be responsible for biological activity other than antigen binding. The Fc portion is apparently responsible for complement fixation, transplacental transfer, binding to cells such as macrophages and granulocytes and the rate of synthesis and catabolism of the immunoglobulin molecule.

Expression of monocyte receptors for monomeric IgG varies widely among patients with ITP as compared with healthy donors. This variation in receptor expression may result from acquired changes in macrophage function or may reflect a more basic genetic disturbance. There is some evidence that the prevalence of ITP may be increased in several genetic subgroups. Abnormalities in the expression of function of Fc(IgG) receptors have been observed in association with certain HLA haplotypes. Moreover, both decreased numbers of C3b receptors (CR1) and uncommon CR1 allotypes have been noted in patients with systemic lupus erythematosus and members of their families. An increase in the number of Fc (IgG) receptors for monomeric IgG has been noted on the monocytes of patients with immune hemolytic anemia. These observations suggest that there may be a fundamental disturbance in the expression of monocyte or macrophage Fc (IgG) receptors in certain patients with ITP or other immunologic disorders.

An increase in the number of density of monocyte or macrophage Fc (IgG) receptors may result from the elaboration of such mediators as gamma interferon during an immune response or infection or the release of bacterial products. Alternatively, a decrease in the number of Fc (IgG) receptors available to bind IgG may result from their occupancy by circulating immune complexes that may be present in patients with ITP.

Autoimmune diseases are those diseases in which the body's mechanisms for distinguishing itself from foreign invaders has malfunctioned in some way. Typically, the body begins to make antibodies to certain parts of itself; these antibodies trigger the immune system which then destroys the tissue identified by the abnormal antibodies. Autoimmune diseases have varied focal points of attack. The autoimmune hemolytic anemias represent a group of disorders in which individuals produce antibodies to one or more of their own erythrocyte membrane antigens. Coating of erythrocytes by the abnormal antibodies is followed by their clearance from the circulation by splenic macrophages and subsequent destruction in the spleen. Representative diseases in this class are immune hemolytic anemia, immune thrombocytopenic purpura and autoimmune neutropenia. Another type of autoimmune disease is the type represented by systemic lupus erythematosus and rheumatoid arthritis. In these diseases, chronic inflammation is present in the joints, tendons, kidneys, lung, heart and other organs. In rheumatoid arthritis, for example, breakdown of joint cartilage into the synovial fluid of the joint is present in later stages of the disease. In systemic lupus erythematosus, however, cartilage or bone degradation is not usually found. Systemic lupus erythematosus and rheumatoid arthritis are often present in conjunction with other types of autoimmune disease. In systemic lupus erythematosus and rheumatoid arthritis, tissue destruction is associated with the presence of IgG-containing complexes in the circulation. It is believed that recognition of these complexes in tissues by cells having Fc receptors initiates or increases tissue destruction by macrophages and possibly other cells such as polymorphonuclear leukocytes in these tissues.

Diseases characterized by interactions of IgG containing immune complexes with macrophage Fc receptors, such as autoimmune diseases, are often chronic and cause much suffering to victims. Treatments currently available have serious side effects.

Corticosteriods inhibit clearance of IgG-coated erythrocytes by modulating splenic macrophage Fc(IgG) receptor activity. They have been used in treating autoimmune disorders such as immune thrombocytopenic purpura and systemic lupus erythematosus. However, corticosteroids have undesirable side effects such as exacerbation of diabetes, hypertension, electrolyte imbalance, increased appetite and weight gain, moonlike faces, osteoporosis, myopathy and increased susceptibility to infection. The severity of these side-effects is related to both the duration and dosage of therapy.

Progesterone has been observed to inhibit splenic macrophage clearance of IgG-coated erythrocytes by fifty percent. Nettl et al, *Blood* 64: Suppl 1:8 A (Abstract) (1984). However, progesterone is a progestational agent, and exerts substantial sex-organ hormonal effects, making its use in treatment less than optimal.

The autoimmune disease chronic immune thrombocytopenic purpura has been treated with danazol, an antigonadotropic drug. Ahn et al, *N. Engl. J. Med.* 308: 1396–1399 (1983); Schreiber et al, *N. Engl. J. Med.* 316: 503–508 (Feb. 26, 1987). Danazol is a synthetic analogue of androgenic steroids and progesterone. As an androgen, danazol can cause masculinization. Moreover, use of this drug in treating systemic lupus erythematosus has been associated with a high incidence of side-effects such as a rise in hepatic enzymes, skin rash, weight gain, acne and myalgia. Dougados et al, *Arthritis Rheum.* (Suppl.) 28: 246 (1985); Jungers et al, *Arthritis Rheum.* 28: 1234–1250 (1985).

The synthetic hydroxyprogesterone derivative, cyproterone acetate has been used in treating female patients having moderately active systemic lupus erythematosus. Jungers et al, supra. Cyproterone acetate is an antigonadotropic agent possessing peripheral antiandrogenic effects. As an antigonadotropic agent, it affords contraception in females. Despite achieving some success in treating systemic lupus erythematosus, it is likely that cyproterone acetate has progestational activity, making it undesirable in treatment. Moreover, it has been reported that antigonadotropic drugs such a cyproterone acetate and danazol should not be used in male systemic lupus erythematosus patients. Jungers et al, supra. In males, the antigonadotropic effect of cyproterone acetate induces a marked decrease in plasma testosterone concentration. In addition, cyproterone acetate acts as an antiandrogen in displacing 5-dihydrotestosterone from a specific receptor in the prostate. According to Jungers et al. supra, administration of cyproterone acetate in male systemic lupus erythematosus patients should induce a marked fall in plasma testosterone level which could potentially provoke an exacerbation of clinically active systemic lupus. Danazol was reported to unmask latent systemic lupus erythematosus in a male patient treated for angioneurotic edema. Fretwell et al, *J. Allergy Clin. Immunol* 69: 306–310 (1982).

The estrogen antagonist/agonist tamoxifen, another candidate for use in treating autoimmune disease, has been observed to enhance the clearance of IgG-coated cells, but to a lesser extent than estradiol alone. Friedman et al., *J. Clin. Invest.* 75:162–167 (1985).

The use of progesterone in inhibiting immune clearance of antibody-coated cells from the circulation, and therefore its potential use in treating disorders such as systemic lupus erythematosus, immune hemolytic anemia and immune thrombocytopenic purpura, is unattractive because of progesterone's sex-organ hormonal effects. There is a need, therefore, for treatments for diseases characterized by interactions of IgG-containing immune complexes with macrophage Fc receptors which have the immune clearance modulating activity of progesterone without the progestational sex-organ hormonal effects of progesterone and the side-effects of other treatments. Accordingly, it is an object of the invention to provide methods of treating these diseases without the undesired effects discussed above and to provide drugs and drug compositions for such uses.

SUMMARY OF THE INVENTION

Methods of modulating the clearance of antibody-coated cells from the circulation of mammals are provided. A compound having the formula

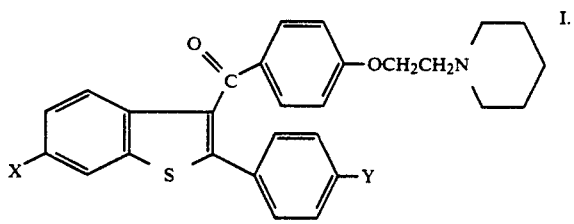

wherein X and Y are independently $OR_1$ or $COR_4$; $R_1$ is hydrogen, $COR_2$ or $R_3$; $R_2$ is hydrogen, $C_1$–$C_{14}$ alkyl, $C_1$–$C_3$ chloroalkyl, $C_1$–$C_3$ fluoroalkyl, $C_5$–$C_7$ cycloalkyl, $C_1$–$C_4$ alkoxy, phenyl, or phenyl mono- or disubstituted with $C_1$–$C_4$ alkyl, $C_1$–$C_4$ alkoxy, hydroxy, nitro, chloro, fluoro or tri(chloro or fluoro) methyl; $R_3$ is $C_1$–$C_4$ alkyl, $C_5$–$C_7$ cycloalkyl or benzyl; and $R_4$ is $C_1$–$C_6$ alkyl; and the physiologically acceptable salts thereof, is administered to the mammal in an amount effective to modulate clearance of antibody-coated cells from the circulation of the mammal.

The invention further provides methods for treatment of mammalian diseases characterized by interactions of IgG-containing immune complexes with macrophage Fc receptors. A compound of formula I is administered to an individual having such disease in an amount effective to modulate the clearance of antibody-coated cells from the circulation of the individual. A physiologically acceptable acid addition salt may alternatively be administered. A preferred compound for use in the invention is keoxifene, whose systematic name is 6-hydroxy-2-(4-hydroxyphenyl)-3-[4-(2-piperidinoethoxy)-benzoyl]benzo[b]thiophene, which is in accordance with formula I where X and Y are independently $OR_1$ and $R_1$ is hydrogen. See formula II.

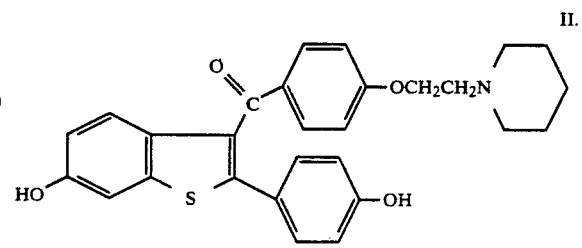

Another preferred compound is 2,2-dimethylpropanonoylkeoxifene which has formula III:

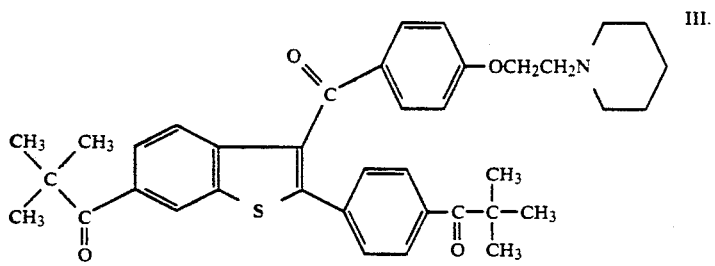

III.

This compound relates to formula I where X and Y are independently $COR_4$ and $R_4$ is tert-butyl.

In preferred embodiments of the invention, modulation of the clearance of antibody-coated cells from the circulation of the mammal is accomplished by inhibiting the clearance of antibody-coated cells from the circulation.

Administration of the preferred compounds provides a method for inhibiting clearance of antibody-coated cells from the circulation of mammals, and thus provides a treatment for mammalian diseases characterized by interactions of IgG-containing immune complexes with macrophage receptors. Such administration may also be useful in a prophylactic context where it is desired to modulate clearance of antibody-coated cells.

In diseases characterized by interactions of IgG-containing immune complexes with macrophage receptors, clearance of antibody-coated erythrocytes may be elevated above normal levels. The compounds preferred for use in the practice of the preferred embodiments of the invention modulate the excessive clearance of antibody-coated cells from the bloodstream of the mammal.

BRIEF DESCRIPTION OF THE DRAWINGS

FIG. 2 is a graph of the clearance of the following $^{51}$Cr-radiolabeled cells from the circulation of guinea pigs as a function of time:
  IgG-coated cells from 2,2-dimethylpropanonyl keoxifene treated animals;
  IgG-coated cells from progesterone and 2,2-dimethylpropanonylkeoxifene treated animals and
  IgG-coated cells from untreated control animals.

DETAILED DESCRIPTION OF THE INVENTION

Figure 1:
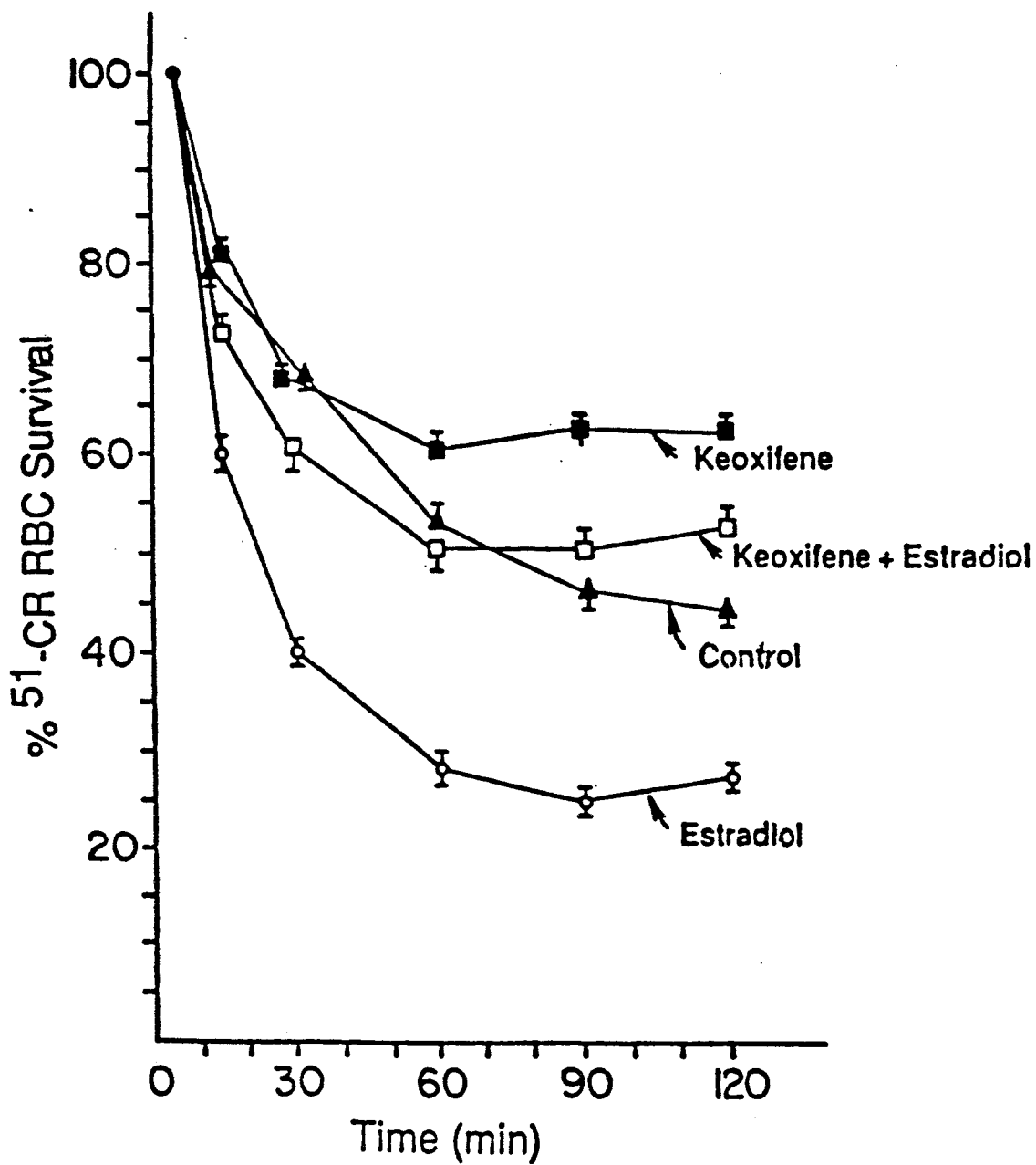
FIG. 1 is a graph of the clearance of the following $^{51}$Cr-radiolabeled cells from the circulation of experimental animals (guinea pigs) and as a function of time:
  IgG-coated guinea pig erythrocytes from untreated control animals (solid triangle data points);
  IgG-coated guinea pig erythrocytes from estradiol-treated animals (open circle data points);
  IgG-coated guinea pig erythrocytes from keoxifene-treated animals (solid square data points);
  IgG-coated guinea pig erythrocytes for animals receiving both estradiol and keoxifene (open square data points).

As used herein, the terms erythrocytes, red blood cells and RBC are equivalent terms for erythrocytes.

Compounds having the formula

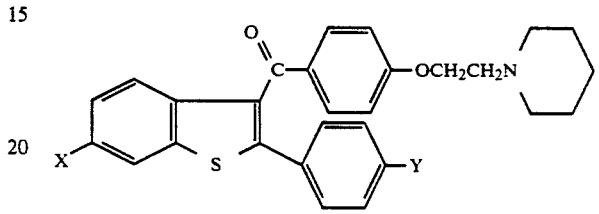

wherein X and Y are independently $OR_1$ or $COR_4$; $R_1$ is hydrogen, $COR_2$ or $R_3$; $R_2$ is hydrogen, $C_1$-$C_{14}$ alkyl, $C_1$-$C_3$ chloroalkyl, $C_1$-$C_3$ fluoroalkyl, $C_5$-$C_7$ cycloalkyl, $C_1$-$C_4$ alkoxy, phenyl, or phenyl mono- or disubstituted with $C_1$-$C_4$ alkyl, $C_1$-$C_4$ alkoxy, hydroxy, nitro, chloro, fluoro or tri(chloro or fluoro) methyl; $R_3$ is $C_1$-$C_4$ alkyl, $C_5$-$C_7$ cycloalkyl or benzyl; and $R_4$ is $C_1$-$C_6$ alkyl; and the physiologically acceptable salts thereof, are suitable for use in the invention. R4 may be any $C_1$-$C_6$ alkyl but is preferably tert butyl.

The preparation of keoxifene, its physiologically acceptable esters and ethers thereof, and physiologically acceptable salts thereof, is disclosed in U.S. Pat. No. 4,418,068, the entire disclosure of which is incorporated herein by reference. The compounds are conveniently made by a process which starts with a benzo[b]-thiophene having a 6-hydroxy group and a 2-(4-hydroxyphenyl) group. The starting compound is protected, acylated and deprotected to form keoxifene. Ethers and esters of keoxifene may then be formed according to the teachings of U.S. Pat. No. 4,418,068. Preferred classes of esters and ethers, and representative compounds, are disclosed in columns 4-6 of U.S.Pat. No. 4,418,068. Keoxifene and salts thereof may be prepared from any of Examples 3-8 and 15-17 of U.S. Pat. No. 4,418,068. Representative esters may be prepared from Examples 9-14. Examples of preferred compounds in the method of the present invention are keoxifene and its physiologically acceptable salts, especially the hydrochloride.

2,2-dimethylpropanonylkeoxifene, another preferred compound for use in the invention, may be prepared by the following method. One part of keoxifene and three parts of triethylamine are mixed in a tetrahydrofuran solvent. The mixture is stirred slowly at room temperature. Two parts of pivaloyl chloride (trimethyl acetic acid) are then added and the mixture stirred. The triethylamine is filtered off and the residue is dried. The residue is then recrystallized to give purified 2,2-dimethylpropanonylkeoxifene.

Keoxifene may be administered in the form of an ester or ether, formed on either or both hydroxy groups. This is possible since, as stated in U.S. Pat. No. 4,418,068, such esters or ethers are believed to be metabolically cleaved in the body, to release the drug compound.

U.S. Pat. No. 4,418,068 discloses the antiestrogenic-/antiandrogenic properties of keoxifene, and physiologically acceptable esters, esters and salts thereof. However, the aforesaid patent does not disclose the activity of keoxifene in inhibiting immune clearance, or suggest its use in treating diseases characterized by interactions between IgG-containing immune complexes and macrophage Fc receptors.

Keoxifene or its physiologically acceptable esters or ethers may be administered in the form of acid addition salts to inhibit immune clearance of antibody-coated cells from the circulation. Such physiologically acceptable addition salts are exemplified by those salts disclosed in U.S. Pat. No. 4,418,068, and include salts which may be formed with inorganic or organic acids such as hydrobromic acid, hydroiodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferably with hydrochloric acid, citric acid, benzoic acid, maleic acid, acetic and propionic acid. Although the free bases may be used, acid addition salts, such as keoxifene HCl, are preferred.

The preferred compounds for use in the invention may be administered in dosage of about 0.05 mg/kg/day to about 50 mg/kg/day of mammal body weight. U.S. Pat. No. 4,418,068 discloses that certain of the compounds which may be useful in the practice of the present invention may be administered in dosage of about 0.05 mg/kg/day to about 50 mg/kg/day of mammal body weight without side effects. While this range of dosage may be used to inhibit immune clearance of antibody-coated cells according to the present invention, a range of about 1.0 to about 20 mg/kg/day is preferred, with about 10 mg/kg/day being most preferred. Immune clearance of antibody-coated cells may be achieved by administering the preferred compounds by any convenient route. Since the compounds are absorbed through the alimentary track, as disclosed in U.S. Pat. No. 4,418,068, oral administration is preferred. The compounds may be formulated as capsules, tablets, troches, suppositories and the like. Accordingly, this invention is also directed to medicaments including the effective compounds in pharmaceutically acceptable carriers. Other forms of administrations such as intravenous and parenteral administration may also be employed. Clinically, keoxifene has been administered to patients at doses approaching 200 mg/day in Phase I trials for end-stage breast carcinoma and in healthy volunteer trials. It is reported that keoxifene has been tolerated well in these trials.

The dosage and dosage regimen is selected to result in clinical response. For example, in the case of autoimmune hemolytic anemia or immune thrombocytopenic purpura, clinical response is evidenced by a rise in blood count. Thus an amount of the compound is administered in dosages and at times effective to modulate clearance, preferably resulting in clinically observable responses. Once a clinical response is achieved and the patient stabilizes, tapering of treatment should begin. This may take several months. Alternate day therapy may be effective in some patients after the clinical course of the disease stabilizes.

Keoxifene is an estrogenic antagonist, with little, if any, sexorgan activity, as shown in U.S. Pat. No. 4,418,068 to Jones. The activity of keoxifene in inhibiting immune clearance indicates an effective treatment for autoimmune diseases involving macrophage clearance of antibody-coated cells, without the harmful side effects accompanying steroid treatment. It is believed that the compounds disclosed herein are useful in treating diseases characterized by interactions of IgG containing immune complexes with macrophage Fc receptors. These include autoimmune disorders such as immune hemolytic anemia, immune thrombocytopenic purpura, and perhaps autoimmune neutropenia. They may also prove to be useful in treating other autoimmune disorders such as systemic lupus erythematosus and rheumatoid arthritis.

It is believed that administration of the preferred compounds modulates the clearance of antibody-coated cells by inhibiting the clearance of IgG-containing immune complexes from the bloodstream which is initiated by interactions of these complexes with macrophage Fc receptors in the spleen of the mammal. It is believed that the compounds useful in the invention modulate the effects of estrogen and estrogen derivatives upon the macrophage Fc receptors. It is also believed that the receptors themselves may be altered or in some way malfunctioning in these diseases which are characterized by interactions of IgG-containing immune complexes with macrophage Fc receptors. The foregoing discussion of likely mechanisms of action is offered with the understanding that the actual mechanism may be different; no limitation of the invention is to be inferred from the discussion of mechanism.

EXAMPLE 1

The immune clearance activity of keoxifene, and thus its utility in treating autoimmune disorders, is demonstrated as follows by an animal model of immune hemolytic anemia established by Schreiber, et al., *J. Clin. Invest.* 51:575 (1972), which is incorporated herein by reference. This animal model has helped to elucidate the effect of corticosteroids in inhibiting the clearance of antibody-coated cells in vivo (see Schreiber et al. supra).

Estradiol and keoxifene were reconstituted in a steroid suspending vehicle consisting of 0.6% carboxymethyl-cellulose, 0.4% Tween 80 (surfactant) and 1.5% ethanol in isotonic saline. Male Hartley guinea pigs weighing 500–600 g (Dutchland Farms, Denver, PA) received injections of estradiol and keoxifene in 1 ml in the dorsal neck fat pad. All animals received a single daily injection of either estradiol, keoxifene, or steroid suspending vehicle along as the sham control. Several animals were given both estradiol and keoxifene at different sites. The animals were studied at the end of a seven day treatment period.

The clearance of IgG-coated erythrocytes was determined in all animals using erythrocytes sensitized with rabbit anti-guinea pig erythrocyte antibody. Rabbit anti-guinea pig erythrocyte antibody was prepared in rabbits according to standard procedures. The IgG fraction was isolated by Sephadex G200 chromatography. Guinea pig erythrocytes were obtained by cardiac puncture, washed, radiolabelled with $^{51}Cr$ sodium chromate (New England Nuclear, Boston, MA) and an aliquot of the radiolabelled erythrocytes was sensitized with rabbit anti-guinea pig erythrocyte IgG so as to coat each cell with approximately 6,000 molecules of IgG antibody per erythrocyte.

$2.7\times10^8$ antibody-coated or control radiolabelled red blood cells were injected intravenously into drug- or sham-treated animals. The clearance of antibody-coated cells was determined by retro-orbital space blood sampling. The percentage of cells remaining in the circulation is calculated according to the formula:

$$\% \text{ Inhibition of Clearance} = 1 - \frac{cpm_c - cpm_x}{cpm_c - cpm_{ea}} \times 100$$

wherein $cpm_c$ is the blood radioactivity in counts per million of untreated control animals injected with unsensitized cells, $cpm_x$ is the blood radioactivity in counts per million of drugtreated animals injected with sensitized cells; and $cpm_{ea}$ is the blood radioactivity in counts per million of the shamtreated animals receiving sensitized cells.

The above formula compares immune clearance in treated animals and untreated animals studied on the same experimental days. It is readily understood that if the effect of a drug treatment is identical to the sham treatment, the mathematical expression is zero. Similarly, 100% inhibition of clearance corresponds to the situation where clearance of IgG-coated cells ($cpm_x$) is identical to that of unsensitized cells ($cpm_c$). Inhibition or enhancement of clearance is indicated by either a positive or negative value of the above expression, respectively.

Separate groups of animals were treated for seven (7) days with (i) 20 mg/kg/day keoxifene, (ii) steroid suspending vehicle (sham), (iii) 1 mg/kg/day estradiol. The effect of keoxifene and estradiol on the clearance of IgG-coated erythrocytes is compared to sham-treated controls in FIG. 1.

While a dose of 1 mg/kg per day of estradiol accelerated the clearance of IgG-coated erythrocytes by 47±16% (p<0.0), when both keoxifene and estradiol were administered, the accelerated clearance caused by estrogen was completely reversed (p<0.0), when both keoxifene and estradiol were administered, the accelerated clearance caused by estrogen was completely reversed (p<0.01); see FIG. 1. This effect was observed at a keoxifene dose of 10 mg/kg per day when given with estradiol at a dose of 1 mg/kg. However, the reversal of clearance was not detected when both keoxifene and estradiol were given at dosages of 1 mg/kg per day.

Daily doses of 10 mg/kg keoxifene for seven (7) days were effective in inhibiting the clearance of IgG-coated erythrocytes in the absence of estradiol treatment. By 60 minutes after injection of sensitized erythrocytes, a dosage of 10 mg/kg per day keoxifene inhibited immune clearance of 7 of 8 animals by 24±4% (p<0.01). By 90 and 120 minutes, this dosage of keoxifene inhibited the clearance of all 8 animals by 39±4% and 42+ ±4%, respectively (p<0.01). Keoxifene in dosages of 1 mg/kg per day also inhibited immune clearance, but only in 2 of the 3 animals tested.

The results indicate that animals receiving keoxifene have impaired immune clearance compared to sham-treated controls. The extent of clearance in animals receiving both estradiol and keoxifene also was remarkably less than those receiving sham treatments.

EXAMPLE 2

2,2-dimethylpropanonylkeoxifene was tested for modulation of the clearance of antibody-coated erythrocytes using the animal model described in Example 1. 2,2-dimethylpropanonylkeoxifene was administered for seven days at a dosage of 10 mg/kg/day. 2,2-dimethylpropanonylkeoxifene and progesterone were administered in combination at a dosage of 10 mg/kg/day each. As shown in FIG. 2, 2,2-dimethylpropanonylkeoxifene inhibited clearance of antibody-coated erythrocytes by 57±1% at 90 minutes and 58±2% at 120 minutes. Animals treated with both 2,2-dimethylpropanonylkeoxifene and progesterone had clearance of antibody-coated red blood cells further inhibited with 48±3% at 90 minutes and 43% 3% clearance at 120 minutes.

What is claimed is:

1. A method of modulating the clearance of antibody-coated cells from the circulation of mammals comprising administering to said mammal an effective amount of a compound of the formula

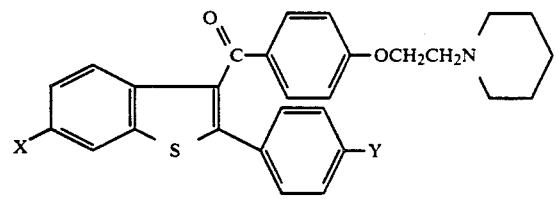

wherein X and Y are independently $OR_1$ or $COR_4$; $R_1$ is hydrogen, $COR_2$ or $R_3$; $R_2$ is hydrogen, $C_1$-$C_{14}$ alkyl, $C_1$-$C_3$ chloroalkyl, $C_1$-$C_3$ fluoroalkyl, $C_5$-$C_7$ cycloalkyl, $C_1$-$C_4$ alkoxy, phenyl, or phenyl mono- or disubstituted with $C_1$-$C_4$ alkyl, $C_1$-$C_4$ alkoxy, hydroxy, nitro, chloro, fluoro or tri(chloro or fluoro) methyl; $R^3$ is $C_1$-$C_4$ alkyl, $C_5$-$C_7$ cycloalkyl or benzyl; and $R_4$ is $C_1$-$C_6$ alkyl; or a physiologically acceptable salt thereof.

2. The method of claim 1 wherein said modulation is inhibition of clearance.

3. The method of claim 1 wherein said antibody-coated cells are IgG-coated cells.

4. The method of claim 1 wherein said antibody-coated cells are antibody-coated erythrocytes.

5. The method of claim 3 wherein said IgG-coated cells are IgG-coated erythrocytes.

6. The method of claim 1 wherein X and Y are $COR_4$.

7. The method of claim 6 wherein $R_4$ is tert-butyl.

8. The method of claim 1 wherein X and Y are independently $OR_1$.

9. The method of claim 8 wherein X and Y are independently hydroxyl.

10. The method according to claim 1 wherein said amount is provided in doses of from about 0.05 mg/kg/day to about 50 mg/kg/day of mammal body weight.

11. The method according to claim 1 wherein said amount is provided in doses of from about 1.0 mg/kg/day to 20 mg/kg/day of mammal body weight.

12. The method according to claim 1 wherein said amount is provided in doses of about 10 mg/kg/day of mammal body weight.

13. A method of treating a mammalian autoimmune disease characterized by interactions of IgG-containing immune complexes with macrophage Fc receptors comprising administering to an individual suspected of having the disease a compound having the formula:

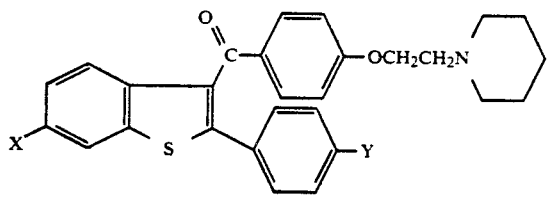

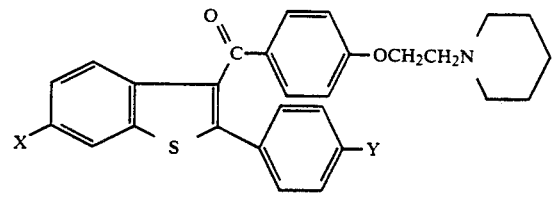

wherein X and Y are independent $OR_1$ or $COR_4$; $R_1$ is hydrogen, $COR_2$ or $R_3$; $R_2$ is hydrogen, $C_1$-$C_{14}$ alkyl, $C_1$-$C_3$ chloroalkyl, $C_1$-$C_3$ fluoroalkyl, $C_5$-$C_7$ cycloalkyl, $C_1$-$C_4$ alkoxy, phenyl, or phenyl mono- or disubstituted with $C_1$-$C_4$ alkoxy, hydroxy, nitro, chloro, fluoro or tri(chloro or fluoro) methyl; $R^3$ is $C_1$-$C_4$ alkyl, $C_5$-$C_7$ cycloalkyl or benzyl; and $R_4$ is $C_1$-$C_6$ alkyl; or physiologically acceptable salt thereof in an amount effective to modulate the clearance by macrophages of antibody-coated cells from the circulation of said mammal.

14. The method of claim 13 wherein said modulation is inhibition of clearance and the amount is an amount effective to inhibit clearance of the antibody-coated cells.

15. The method of claim 13 wherein said antibody-coated cells are IgG-coated cells.

16. The method of claim 13 wherein said antibody-coated cells are antibody-coated erythrocytes.

17. The method of claim 15 wherein said IgG-coated are IgG-coated erythrocytes.

18. The method of claim 13 wherein X and Y are $COR_4$.

19. The method of claim 18 wherein $R_4$ is tert-butyl.

20. The method of claim 13 wherein X and Y are independently $OR_1$.

21. The method of claim 20 wherein X and Y are independently hydroxyl.

22. The method according to claim 13 wherein said amount is provided in doses of from about 0.05 mg/kg/day to about 50 mg/kg/day of mammal body weight.

23. The method according to claim 13 wherein said amount is provided in doses of from about 1.0 mg/kg/day to 20 mg/kg/day of mammal body weight.

24. The method according to claim 13 wherein said amount is provided in doses of about 10 mg/kg/day of mammal body weight.

25. A method according to claim 13 wherein the disease is immune thrombocytopenic purpura.

26. A method according to claim 13 wherein the disease is immune hemolytic anemia.

27. A method according to claim 13 wherein the disease is systemic lupus erythematosus.

28. A method according to claim 13 wherein the disease is rheumatoid arthritis.

29. The use in the manufacture of a medicament for treating an autoimmune disease of a composition in accordance with the formula:

wherein X and Y are independent $OR_1$ or $COR_4$; $R_1$ is hydrogen, $COR_2$ or $R_3$; $R_2$ is hydrogen, $C_1$-$C_{14}$ alkyl, $C_1$-$C_3$ chloroalkyl, $C_1$-$C_3$ fluoroalkyl, $C_5$-$C_7$ cycloalkyl, $C_1$-$C_4$ alkoxy, phenyl, or phenyl mono- or disubstituted with $C_1$-$C_4$ alkyl, $C_1$-$C_4$ alkoxy, hydroxy, nitro, chloro, fluoro or tri(chloro or fluoro) methyl; $R^3$ is $C_1$-$C_4$ alkyl, $C_5$-$C_7$ cycloalkyl or benzyl; and $R_4$ is $C_1$-$C_6$ alkyl; or physiologically acceptable salt thereof.

30. The method of claim 29 wherein X and Y are $COR_4$.

31. The method of claim 30 wherein $R_4$ is tert-butyl.

32. The method of claim 29 wherein X and Y are independently $OR_1$.

33. The method of claim 32 wherein X and Y are independently hydroxyl.

34. The use in the manufacture of a medicament for treating immune thrombocytopenic purpurea of a composition in accordance with the formula:

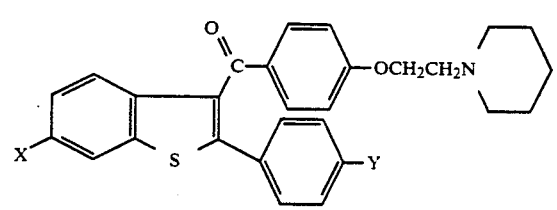

wherein X and Y are independent $OR_1$ or $COR_4$; $R_1$ is hydrogen, $COR_2$ or $R_3$; $R_2$ is hydrogen, $C_1$-$C_{14}$ alkyl, $C_1$-$C_3$ chloroalkyl, $C_1$-$C_3$ fluoroalkyl, $C_5$-$C_7$ cycloalkyl, $C_1$-$C_4$ alkoxy, phenyl, or phenyl mono- or disubstituted with $C_1$-$C_4$ alkyl, $C_1$-$C_4$ alkoxy, hydroxy, nitro, chloro, fluoro or tri(chloro or fluoro) methyl; $R^3$ is $C_1$-$C_4$ alkyl, $C_5$-$C_7$ cycloalkyl or benzyl; and $R_4$ is $C_1$-$C_6$ alkyl; or physiologically acceptable salt thereof.

35. The use of claim 34 wherein X and Y are $COR_4$.

36. The use of claim 35 wherein $R_4$ is tert-butyl.

37. The use of claim 34 wherein X and Y are independently $OR_1$.

38. The use of claim 37 wherein X and Y are independently hydroxyl.

39. The use in the manufacture of a medicament for treating immune hemolytic anemia of a composition in accordance with the formula:

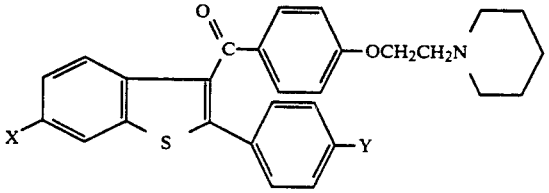

wherein X and Y are independent $OR_1$ or $COR_4$; $R_1$ is hydrogen, $COR_2$ or $R_3$; $R_2$ is hydrogen, $C_1$-$C_{14}$ alkyl, $C_1$-$C_3$ chloroalkyl, $C_1$-$C_3$ fluoroalkyl, $C_5$-$C_7$ cycloalkyl, $C_1$-$C_4$ alkoxy, phenyl, or phenyl mono- or disubstituted with $C_1$-$C_4$ alkyl, $C_1$-$C_4$ alkoxy, hydroxy, nitro, chloro, fluoro or tri(chloro or fluoro) methyl; $R^3$ is $C_1$-$C_4$ alkyl, $C_5$-$C_7$ cycloalkyl or benzyl; and $R_4$ is $C_1$-$C_6$ alkyl; or physiologically acceptable salt thereof.

40. The use of claim 39 wherein X and Y are $COR_4$.

41. The use of claim 40 wherein $R_4$ is tert-butyl.

42. The use of claim 39 wherein X and Y are independently $OR_1$.

43. The use of claim 42 wherein X and Y are independently hydroxyl.

44. The use in the manufacture of a medicament for treating systemic lupus erythematosus of a composition in accordance with the formula:

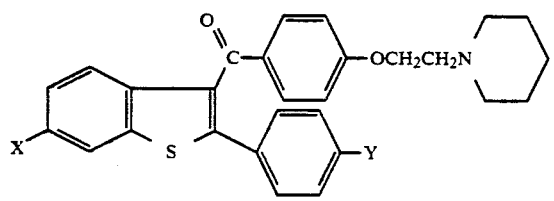

wherein X and Y are independent $OR_1$ or $COR_4$; $R_1$ is hydrogen, $COR_2$ or $R_3$; $R_2$ is hydrogen, $C_1$-$C_{14}$ alkyl, $C_1$-$C_3$ chloroalkyl, $C_1$-$C_3$ fluoroalkyl, $C_5$-$C_7$ cycloalkyl, $C_1$-$C_4$ alkoxy, phenyl, or phenyl mono- or disubstituted with $C_1$-$C_4$ alkyl, $C_1$-$C_4$ alkoxy, hydroxy, nitro, chloro, fluoro or tri(chloro or fluoro) methyl; $R^3$ is $C_1$-$C_4$ alkyl, $C_5$-$C_7$ cycloalkyl or benzyl; and $R_4$ is $C_1$-$C_6$ alkyl; or physiologically acceptable salt thereof.

45. The use of claim 44 wherein X and Y are $COR_4$.

46. The use of claim 45 wherein $R_4$ is tert-butyl.

47. The use of claim 44 wherein X and Y are independently $OR_1$.

48. The use of claim 47 wherein X and Y are independently hydroxyl.

49. The use in the manufacture of a medicament for treating immune thrombocytopenic purpurea of a composition in accordance with the formula:

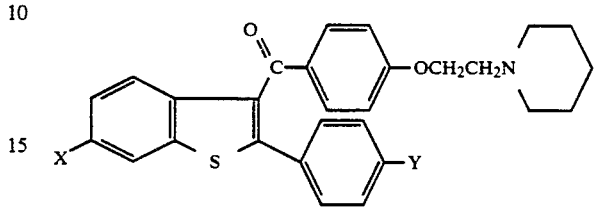

wherein X and Y are independent $OR_1$ or $COR_4$; $R_1$ is hydrogen, $COR_2$ or $R_3$; $R_2$ is hydrogen, $C_1$-$C_{14}$ alkyl, $C_1$-$C_3$ chloroalkyl, $C_1$-$C_3$ fluoroalkyl, $C_5$-$C_7$ cycloalkyl, $C_1$-$C_4$ alkoxy, phenyl, or phenyl mono- or disubstituted with $C_1$-$C_4$ alkyl, $C_1$-$C_4$ alkoxy, hydroxy, nitro, chloro, fluoro or tri(chloro or fluoro) methyl; $R^3$ is $C_1$-$C_4$ alkyl, $C_5$-$C_7$ cycloalkyl or benzyl; and $R_4$ is $C_1$-$C_6$ alkyl; or physiologically acceptable salt thereof.

50. The use of claim 49 wherein X and Y are $COR_4$.

51. The use of claim 50 wherein $R_4$ is tert-butyl.

52. The use of claim 49 wherein X and Y are independently $OR_1$.

53. The use of claim 52 wherein X and Y are independently hydroxyl.

* * * * *